United States Patent [19]

Rueppel et al.

[11] 4,227,888

[45] Oct. 14, 1980

[54] METHOD FOR THE QUANTITATIVE DETERMINATION OF CYANIDE

[75] Inventors: Melvin L. Rueppel, Kirkwood; Chihyuan C. Ting, Creve Coeur, both of Mo.

[73] Assignee: Monsanto Company, St. Louis, Mo.

[21] Appl. No.: 970,689

[22] Filed: Dec. 18, 1978

[51] Int. Cl.$^2$ ................. G01N 31/22; G01N 33/18
[52] U.S. Cl. ................................................. 23/230 R
[58] Field of Search ...................................... 23/230 R

[56] References Cited

U.S. PATENT DOCUMENTS

| | | | |
|---|---|---|---|
| 3,147,082 | 9/1964 | Thompson | 23/230 R |
| 3,195,983 | 7/1965 | Platte | 23/230 R |
| 3,505,217 | 4/1970 | Morico | 210/59 |

FOREIGN PATENT DOCUMENTS

| | | | |
|---|---|---|---|
| 49-106588 | 10/1974 | Japan | 422/5 |
| 1150096 | 4/1969 | United Kingdom | 210/59 |

OTHER PUBLICATIONS

"Standard Methods for the Examination of Water & Wastewater", 14th ed. (1975), pp. 361–387.
"Annual Book of ASTM Standards", Part 23, pp. 498–507 (1973).

*Primary Examiner*—Arnold Turk
*Attorney, Agent, or Firm*—Steven M. Odre; Donald W. Peterson

[57] ABSTRACT

A method for quantitatively determining the cyanide content of aqueous solution containing aldehydes and/or ketones as a measure of the sum of the free cyanide and cyanohydrin content. The method comprises converting cyanohydrin to free cyanide and then determining the free cyanide content of the solution.

9 Claims, No Drawings

METHOD FOR THE QUANTITATIVE DETERMINATION OF CYANIDE

The invention relates to a method for quantitatively determining cyanide present both as free cyanide and cyanohydrin in aqueous solutions containing aldehydes and/or ketones. More particularly, the invention is concerned with a method of determining cyanide at concentrations as low as 20 parts cyanide per billion parts water in solutions containing aldehydes and/or ketones.

Conventional methods for determining cyanide are effective in measuring only the free cyanide content of a sample. The term "free cyanide" as used herein includes cyanide ion and cyanide complexes which are easily hydrolyzed to hydrogen cyanide. These methods are described in *Standard Methods for the Examination of Water and Wastewater*, 14th Edition (1975) page 361; *Annual Book of ASTM Standards*, Parts 23 (1973) and *U.S. EPA Technology Transfer*, EPA-625-16-74-003, page 40, and include potentiometric analysis utilizing a cyanide ion selective electrode; colorimetric analysis employing pyridine-barbituric acid reagent for color development and titrimetric analysis using silver nitrate with a paradimethylaminobenzalrhodanine indicator. However, as currently practiced, these methods are unable to accurately measure the cyanide level in solutions containing aldehydes and/or ketones since these compounds react with cyanide to produce cyanohydrins which are hydrolyzed to ammonia rather than to dydrogen cyanide. Distillation techniques such as those described by Royer et al in *Analytical Letters*, 6(7), 619–627 (1973) while commonly employed to remove interfering substances in conventional cyanide analysis, will produce low cyanide measurements when aldehydes or ketones are present in the sample since any cyanohydrins which are produced are readily converted to ammonia and related decomposition products under distillation conditions.

Hikaru Watanabe et al in Japan Kokai 74, 106, 558 disclose the use of hydrazine derivatives as effective agents in removing formaldehyde odor from curable amino alkyd resins.

Compounds that interfere with conventional methods for quantitatively determining cyanide include aldehydes or ketones having an equilibrium constant that favors the reaction of the aldehyde or ketone with cyanide to produce a cyanohydrin. Examples include aliphatic or aromatic aldehydes such as formaldehye, acetaldehyde and benzaldehyde as well as ketones such as acetone, methylethylacetone and cyclohexanone.

A method for quantitatively determining cyanide in the presence of aldehydes or ketones is of particular importance in monitoring the cyanide content of industrial waste solutions. Techniques for detoxicating cyanide containing waste solutions as described in British Pat. No. 1,150,096 and U.S. Pat. No. 3,505,217 utilize a large excess of an aldehyde or ketone preferably formaldehyde to convert any cyanide to a non-toxic product in order to render the waste solution suitable for discharge. The conversion involves a two-step process and is generally illustrated by the following reaction scheme utilizing formaldehyde as the aldehyde.

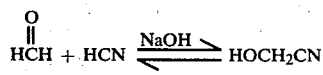

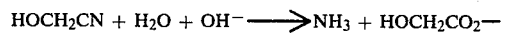

Initially, formaldehyde reacts with cyanide in the presence of a base to produce cyanohydrin. If the formaldehyde is in excess, the cyanohydrin is subsequently hydrolyzed in the presence of a base to ammonia, thus detoxicating the waste solution. Due to the wide-spread use of such waste treatment techniques and the high level of toxicity of cyanohydrins, in order to insure safe levels of cyanide exposure in waste solutions, it is necessary to have an analytical system that will determine on a continuous basis quantities of cyanide which may be present both as free cyanide and in the form of cyanohydrin.

The present invention provides a method which continuously if desired, accurately measures the cyanide content of solutions containing aldehydes or ketones. This method provides for the determination of the cyanide content of a solution based on the total of the free cyanide and cyanohydrin content present in the solution. This method is particularly effective in determining the amount of cyanide in the presence of a large excess of aldehydes or ketones, such as is present in treated cyanide containing waste streams.

In accordance with the method of the present invention, an aqueous sample containing free cyanide and/or cyanohydrin in the presence of aldehydes or ketones is treated with a compound of the formula $$R-NH_2 \qquad (I)$$

wherein R is hydroxyl, lower alkoxy and

wherein $R_1$ and $R_2$ are independently hydrogen or any radical which does not contain groups capable of being hydrolyzed to hydrogen cyanide; as well as hydrates and acid salts thereof. It is preferred that R is

wherein $R_1$ and $R_2$ are independently hydrogen; lower alkyl; hydroxyl; phenyl; phenyl substituted with up to three groups individually selected from the class consisting of lower alkyl, lower alkoxy and halogen; and substituted carbonyl wherein the carbonly is substituted with groups selected from the class consisting of hydroxyl, lower alkyl, amino, lower alkylamino, phenyl and phenyl substituted with up to three groups individually selected from the class consisting of lower alkyl, lower alkoxy and halogen. The pH of the sample is then adjusted to a level sufficient to convert cyanohydrin to free cyanide. The free cyanide is then measured as an indication of the cyanide content of the sample.

As employed herein, the term "lower" designates those radicals which have up to four carbon atoms in a straight or branched chain. Groups representative of these radicals include for example, methyl, ethyl, propyl, isopropyl, butyl, isobutyl, t-butyl and the like.

The term "halogen" as used herein includes chloro, bromo, fluoro and iodo.

Examples of compounds that may effectively be employed in the method of the present invention to remove aldehydes and ketones include hydrazine; mono- and di-hydroxylhydrazine; mono- di-alkylhydrazines such as methylhydrazine, dimethylhydrazine and methylethylhydrazine; hydroxylalkylhydrazines such as hydroxylethylhydrazine and phenylhydrazine.

Illustrative of compounds of Formula (I) wherein $R_1$ and $R_2$ are substituted phenyl groups, include 4-methylphenylhydrazine, 3-ethoxyphenylhydrazine, 4-chlorophenylhydrazine, 4-ethyl-3-methylphenylhydrazine, 2-chloro-4-methylphenylhydrazine, 2-methyl-3-ethoxyphenylhydrazine and the like.

Examples of compound of Formula (I) wherein $R_1$ and $R_2$ are substituted carbonyl groups include acetylhydrazide, semicarbazide, glycolhydrazide, methylaminocarbonylhydrazide, phenylaminocarbonylhydrazide, 4-methylphenylaminocarbonylhydrazide and the like.

Also effective in removing aldehydes and ketones are dioic acid hydrazines such as malic acid hydrazide, malonic acid hydrazide, succinic acid hydrazide, tartaric acid hydrazide, isophthalic acid hydrazide, adipic acid hydrazide, sebacid acid hydrazide and the like.

In general, to provide water solubility, neither the $R_1$ or $R_2$ groups should contain more than about 12 carbon atoms. For ease of reaction and economic considerations, hydrazine is preferred.

In order to optimize the accuracy of the cyanide determination of the present invention, the amount of a compound of Formula (I) used to remove any aldehyde or ketone should be at least equal to the total aldehyde and ketone content of the sample solution. The total aldehyde and ketone content is the sum of the concentration of any excess unreacted aldehyde or ketone plus the concentration of any aldehyde or ketone that has reacted with cyanide to form the cyanohydrin. For maximum accuracy, it is preferred to employ an amount of a compound of Formula (I) which is in excess of that required to completely react with the total content of aldehydes and ketones.

The removal of aldehydes and ketones is illustrated by the following reaction utilizing formaldehyde as the aldehyde:

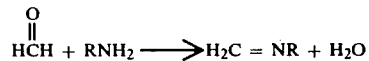

Although not narrowly critical, a reaction time of 5 minutes is generally sufficient to react any excess unreacted aldehyde or ketone with a compound of Formula (I).

Following the removal of any aldehyde or ketone by treating a sample solution with a compound of Formula (I), it is critical that the pH of the sample solution then be adjusted to a level sufficient to convert any cyanohydrin to free cyanide as illustrated by the following reaction:

A pH greater than 7 is generally sufficient to convert cyanohydrin to free cyanide. To minimize reaction time and maximize the conversion of cyanohydrin to free cyanide a pH in the range of 11-12 is preferred.

To adjust the pH level, bases that ionize in water to form a hydroxyl ion and not interfere with the method are employed. Examples include sodium hydroxide, potassium hydroxide and the like.

Although not narrowly critical the reaction time at the adjusted pH should be a period sufficient to completely convert the cyanohydrin to free cyanide. At a pH range of 11-12, a reaction time of 5 minutes has been found to be sufficient.

Upon the removal of aldehydes and ketones and conversion of cyanohydrin to free cyanide, the free cyanide content of the sample solution is determined using any conventional method of determining cyanide.

Although any conventional method may be employed to measure the free cyanide content, the present invention is best utilized in connection with the colormetric procedure using pyridine-barbituric acid for color development. In this procedure, the sample, after removal of any aldehyde and/or ketone and conversion of cyanohydrin to free cyanide, is acidified with 10% phosphoric acid in order to convert the free cyanide to hydrogen cyanide. The hydrogen cyanide thus formed is diffused across a gas permeable membrane and is absorbed in dilute sodium hydroxide. The cyanide ion is then reacted with chloroamine-T to form cyanogen chloride which is subsequently reacted with pyridine and barbituric acid to form a red complex. The absorbance is recorded at a wavelength of 570 nm. Amounts of cyanide as low as 20 parts per billion can be measured in this manner. Concentration of cyanide greater than 1,000 parts per billion require dilution before the colorimeter analysis. A range between 0.02-1.00 parts per million can be measured.

The colorimetric procedure can be employed utilizing a Technicon "Autoanalyzer ®" as illustrated in Example 1 using hydrazine to remove aldehydes and/or ketones. The preparations of the reagents in the following example are well known to one skilled in the art and are fully described in Technicon Industrial Method No. 353-75 W/A.

All reagents are introduced into the analyzer flow system by means of a peristalic pump. The flow rates, concentrations of the reagents and other variable parameters are only shown to exemplify the method of the present invention and are not to be considered limitations thereof.

EXAMPLE 1

Reagents
95% Hydrazine
0.01 N Sodium Hydroxide
1.0 N Sodium Hydroxide
10% Phosphoric acid (v/v)
Buffered chloroamine-T - prepared by adding 200 ml of 0.4% Chloroamine-T solution to 800 ml of phosphate buffer solution (pH 5.2) and mixing thoroughly
Pyridine-Barbituric acid reagent.

Procedure

A sample stream pumping at a rate of 3.9 ml/min containing the cyanide to be determined was segmented by air bubbles. To the sample stream was added 95% hydrazine pumping at a rate of 0.015 ml/min and to insure completeness of reaction, the sample stream was passed through a mixing coil having a residence time of 5 minutes. The sample stream was debubbled and again segmented by air bubbles. To the sample stream pumping at a rate of 3.4 ml/min was added 0.01 N sodium hydroxide at a rate of 1.2 ml/min. Again to insure completeness of reaction, the sample stream was passed through a mixing coil having a residence time of 5 minutes. The sample stream was debubbled and again segmented by air bubbles. To the sample stream pumping at a rate of 3.9 ml/min which now contans cyanide predeminately in the form of free cyanide was added 10% phosphoric acid at a rate of 0.42 ml/min. The resultant sample stream now containing hydrogen cyanide was then dialyzed into a receiving stream which consists of 0.01 N sodium hydroxide pumped at a rate of 0.42 ml/min.

The stream containing the undialyzed material was added to 1.0 N sodium hydroxide before discarding.

After dialysis, the hydrogen cyanide in the receiving solution was reacted with buffered chloroamine-T pumping at a rate of 0.42 ml/min to produce cyanogen chloride. To insure a complete reaction, the cyanogen chloride stream was passed through a mixing coil. To this stream was then added pyridinebarbituric acid reagent at a rate of 0.42 ml/min producing a blue-red dye. To optimize color development of the dye stream, it was passed through a mixing coil and then through a heating bath at 37° C. The stream was debubbled and the absorbance of the dye complex was measured at a wavelength of 570 nm in a photometer equipped with a flow-through cell.

After calibration with a cyanide standard of known concentration, cyanide concentrations of unknown specimens can be determined using this method.

If the apparatus is connected to a sampler, it becomes possible to determine 30 different samples per hour. It is also possible to connect the sample input line directly to a waste treatment reservoir and continuously monitor the cyanide content of the waste solution.

Upon removal of aldehydes or ketones and the conversion of cyanohydrin to free cyanide, the free cyanide content of the sample may also be determined using any other conventional method which in principle can measure free cyanide. For example, a potentiometric analysis using a cyanide ion selective electrode with 0.1 N sodium hydroxide as the ionic strength adjustor can measure 0.1–100 part per million cyanide. For cyanide concentrations greater than 1 part per million, a titrimetric procedure utilizing silver nitrate with paradimethylaminobenzalrhodanine indicator can be employed to measure the free cyanide content. Another alternative is to utilize a gas chromatograph equipped with an electron capture or nitrogenphosphorus detector to measure the free cyanide content. The conditions necessary to practice these methods are set forth in the publications previously mentioned, and any other variables can readily be determined by one skilled in the art.

It is well understood by those skilled in the art that the range of cyanide that may be measured in each procedure is not limiting since larger amounts of cyanide can be determined using proper dilution of the original sample.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method for quantitatively determining the cyanide content of a solution containing interfering aldehydes and/or ketones which comprises sequentially the steps of
    (a) treating the solution with an amount of a compound of the formula

R - NH$_2$ wherein R is selected from the group consisting of hydroxyl, lower alkoxy and

wherein R$_1$ and R$_2$ are independently hydrogen or any radical which does not contain groups capable of being hydrolyzed to hydrogen cyanide; sufficient to react with the total aldehyde and ketone content;
    (b) maintaining the pH of the solution at a level sufficient to convert any cyanohydrin to free cyanide,
    (c) means for quantitatively determining the level of free cyanide as a measure of the cyanide content of the solution.

2. A method according to claim 1 which comprises as step (a) treating the solution with a compound of the formula

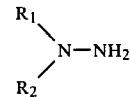

wherein R$_1$ and R$_2$ are independently selected from the group consisting of hydrogen; lower alkyl; hydroxyl; phenyl; phenyl substituted with up to three groups individually selected from the class consisting of lower alkyl, lower alkoxy and halogen; and substituted carbonyl wherein the carbonyl is substituted with groups selected from the class consisting of hydroxyl, lower alkyl, amino, lower alkylamino, phenyl and phenyl substituted with up to three groups individually selected from the class consisting of lower alkyl, lower alkoxy and halogen.

3. A method according to claim 2 which comprises treating the solution with hydrazine.

4. A method according to claim 1 which comprises maintaining the pH at a level of 7 or greater 5. A method according to claim 4 which comprises maintaining the pH in the range of 11–12.

6. A method according to claim 1 which maintaining comprises adjusting the pH level using sodium hydroxide.

7. A method according to claim 1 wherein said means for quantitatively determining the free cyanide comprises sequentially the steps of
    (a) converting the free cyanide to hydrogen cyanide using phosphoric acid,
    (b) reacting the hydrogen cyanide with chloroamine-T to produce cyanogen chloride,
    (c) reacting the cyanogen chloride with barbituric acid and pyridine to form a complex, (d) photometrically determining the absorbance of the complex as a measure of the total cyanide present initially, provided that the solution has been heated with a compound other than phenylhydrazine to remove the aldehydes and ketones.

8. A method according to claim 7 which comprises
 (a) treating the solution with an amount of hydrazine sufficient to react with the total aldehyde and ketone content,
 (b) adjusting the pH to a range of 11–2 using sodium hydroxide.

9. A method according to claim 1 wherein said means for quantitatively determining the free cyanide comprises a cyanide ion selective electrode.

* * * * *